United States Patent
Onik

Patent Number: 5,693,011
Date of Patent: Dec. 2, 1997

[54] SURGICAL SUCTION CUTTING INSTRUMENT

[75] Inventor: Gary M. Onik, Orlando, Fla.

[73] Assignee: Surgical Dynamics, Inc., Norwalk, Conn.

[21] Appl. No.: 429,662

[22] Filed: Apr. 27, 1995

[51] Int. Cl.$^6$ .................................................. A61M 1/00
[52] U.S. Cl. .................................................. 604/22; 604/280
[58] Field of Search .................................. 604/266–268, 604/280, 264; 606/167–172; 128/751–758

[56] References Cited

U.S. PATENT DOCUMENTS

| | | |
|---|---|---|
| Re. 33,258 | 7/1990 | Onik et al. . |
| 3,308,825 | 3/1967 | Cruse .................................. 604/267 |
| 3,606,878 | 9/1971 | Kellogg, Jr. . |
| 3,623,483 | 11/1971 | Dyer, Jr. ............................. 604/266 |
| 4,099,529 | 7/1978 | Peyman . |
| 4,111,207 | 9/1978 | Seiler, Jr. . |
| 4,158,916 | 6/1979 | Adler .................................. 604/268 |
| 4,228,802 | 10/1980 | Trott .................................. 604/267 |
| 4,246,902 | 1/1981 | Martinez . |
| 4,282,884 | 8/1981 | Boebel . |
| 4,321,921 | 3/1982 | Laszczower ......................... 604/35 |
| 4,513,745 | 4/1985 | Amoils . |
| 4,589,414 | 5/1986 | Yoshida et al. . |
| 4,601,724 | 7/1986 | Hooven et al. ..................... 604/266 |
| 4,603,694 | 8/1986 | Wheeler . |
| 4,620,547 | 11/1986 | Boebel . |
| 4,651,753 | 3/1987 | Lifton . |
| 4,767,404 | 8/1988 | Renton ................................ 604/268 |
| 4,777,948 | 10/1988 | Wright . |
| 4,850,354 | 7/1989 | McGurk-Burleson et al. . |
| 4,955,887 | 9/1990 | Zirm . |
| 4,961,430 | 10/1990 | Sheahon . |
| 5,031,634 | 7/1991 | Simon . |
| 5,042,461 | 8/1991 | Inoue et al. ....................... 604/266 |
| 5,106,364 | 4/1992 | Hayafuji et al. . |
| 5,176,628 | 1/1993 | Charles et al. . |
| 5,226,910 | 7/1993 | Kajiyama et al. . |
| 5,250,065 | 10/1993 | Clement et al. . |
| 5,261,885 | 11/1993 | Lui ..................................... 604/266 |
| 5,269,797 | 12/1993 | Bonati et al. . |
| 5,285,795 | 2/1994 | Ryan et al. . |
| 5,290,303 | 3/1994 | Pingleton et al. . |
| 5,439,474 | 8/1995 | Li . |
| 5,569,284 | 10/1996 | Young et al. ....................... 604/22 |

FOREIGN PATENT DOCUMENTS

| | | | |
|---|---|---|---|
| 0887228 | 11/1971 | Canada ............................... 604/268 |
| 432363 | 6/1991 | European Pat. Off. ............. 604/268 |
| 331581 | 1/1921 | Germany ............................. 604/268 |
| 184829 | 6/1985 | Germany . |
| 8500526 | 2/1985 | WIPO ................................. 604/266 |

*Primary Examiner*—Manuel Mendez

[57] ABSTRACT

A surgical suction cutting instrument is provided with a suction port. A guard is mounted at the suction port to permit material to enter the suction port while preventing vital structures such as nerves, vessels and dura from entering the port and being damaged during the cutting operation.

16 Claims, 3 Drawing Sheets

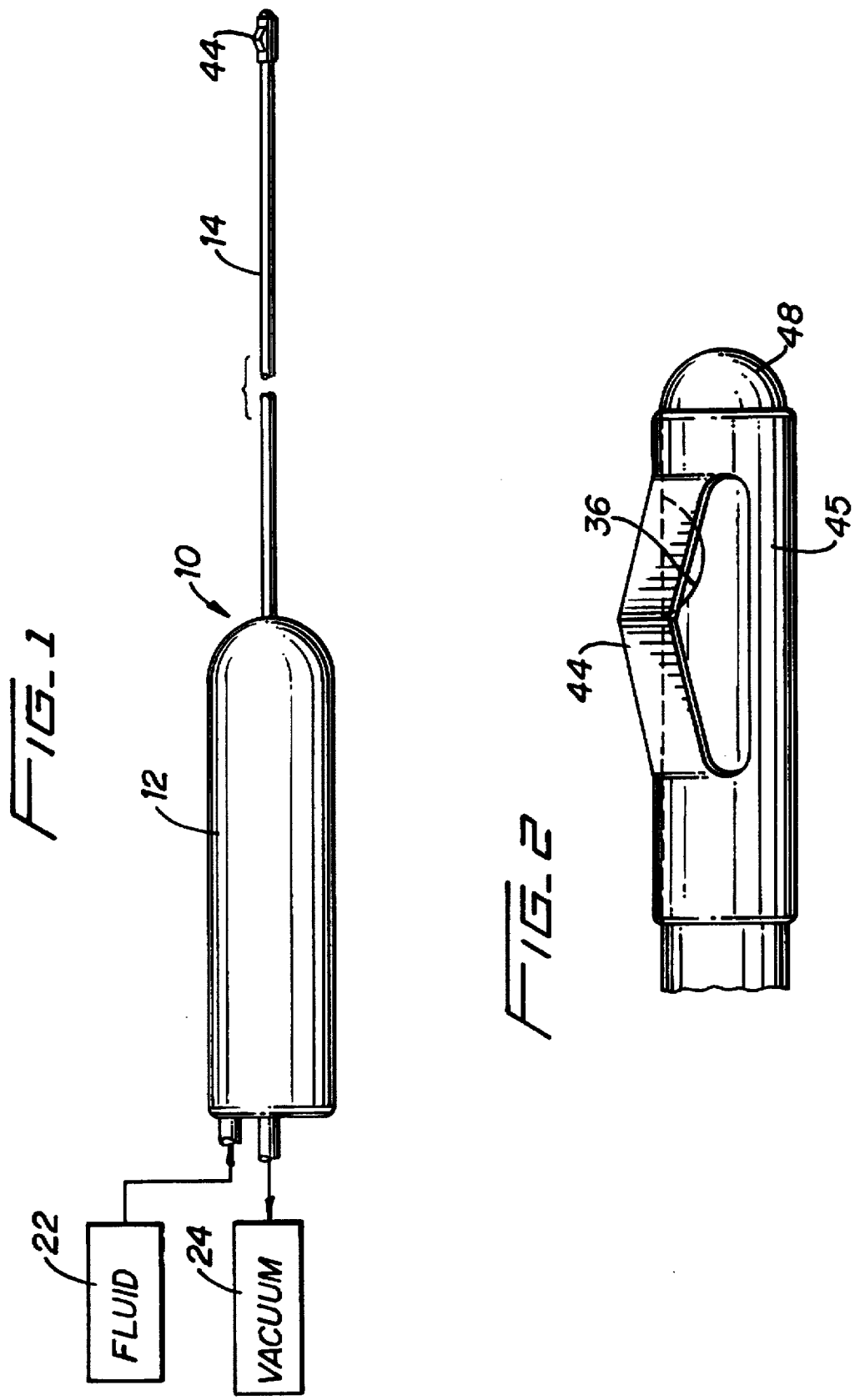

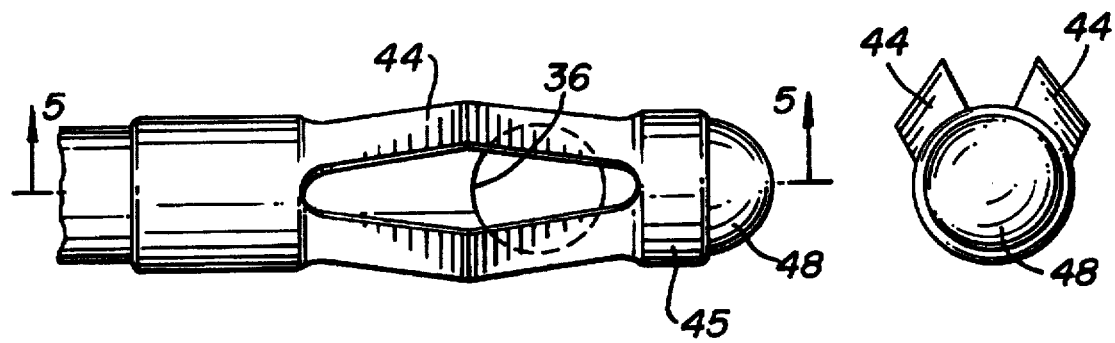
FIG. 3
FIG. 4
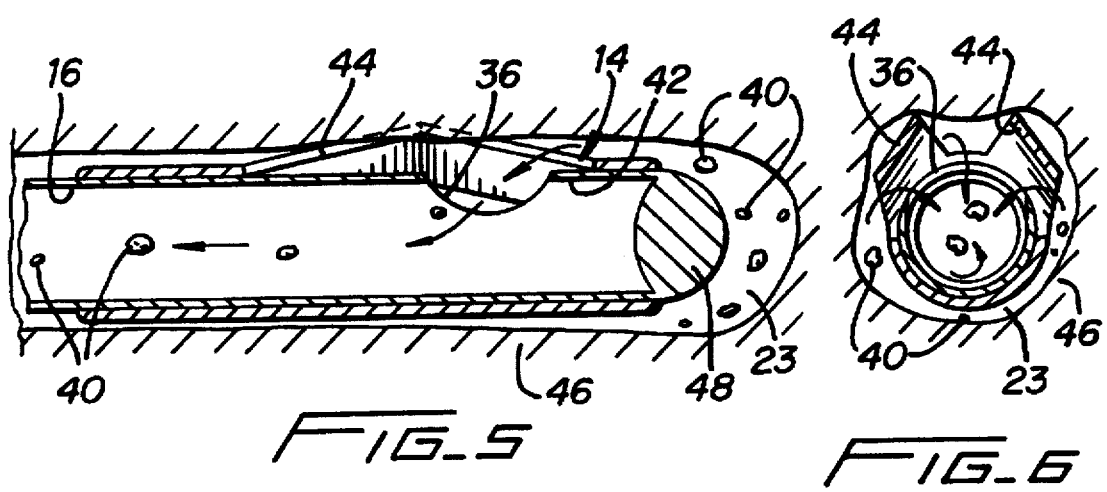
FIG. 5
FIG. 6
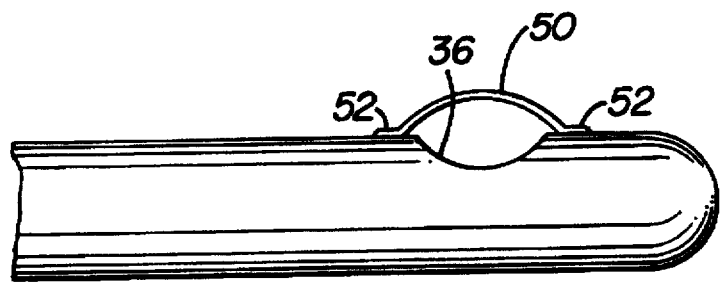
FIG. 7

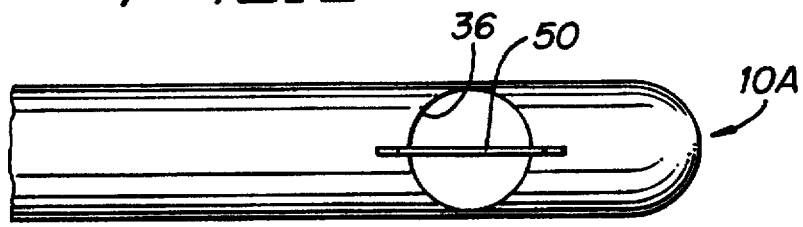
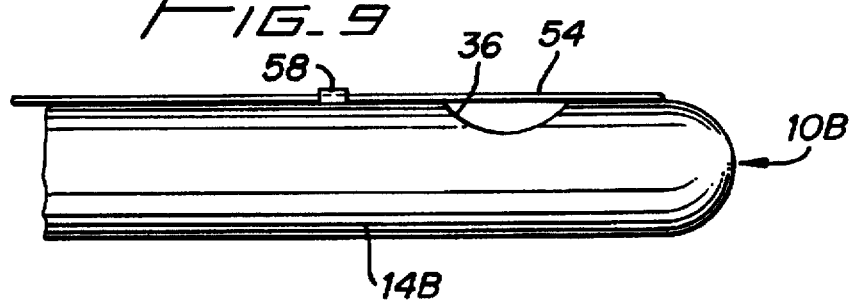
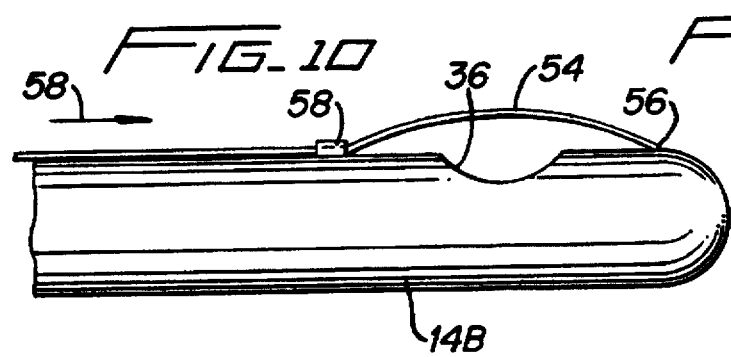
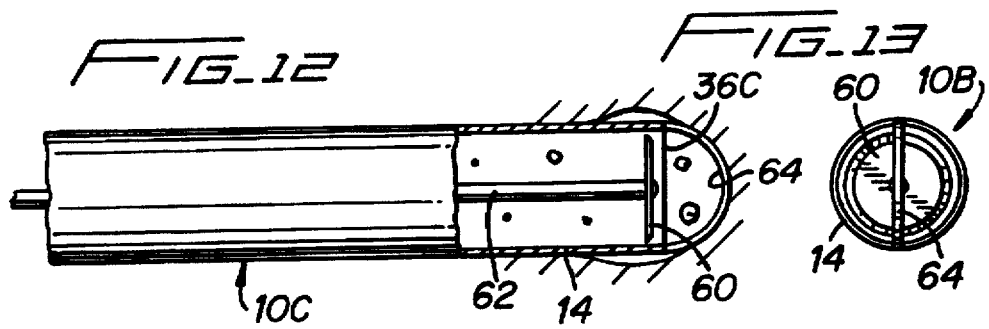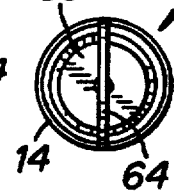
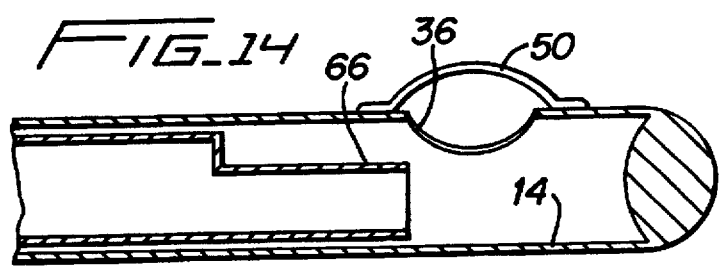

SURGICAL SUCTION CUTTING INSTRUMENT

BACKGROUND OF THE INVENTION

The present invention relates to surgical suction cutting instruments which have a suction port through which material to be removed enters the instrument. There are various known types of surgical cutting instruments such as used for arthroscopy shavers, laparoscopic tissue morcilators, disc aspiration and the like. One of the dangers in the use of such instruments is that during aspiration the suction used for removing the material through the suction port may also cause vital structures, such as nerves, vessels and dura or the specimen bag, to be sucked into the probe and thereby become damaged.

In many areas of surgery such suction cutting instruments are in use where it would be an advantage to automatically remove movable, or deformable material safely without the risk of damaging other structures. These structures such as nerves, vessels and dura are generally tethered on both ends. It would also be desirable if some means could be provided for limiting the possibility of limiting these vital structures from entering the suction port of the surgical suction cutting instrument. It would be desirable to incorporate these means in various known surgical suction cutting instruments such as a rotary design cutter used in standard arthroscopic shavers as well as instruments used for disc aspiration such as reciprocating cutters. Known devices are described in U.S. Pat. Nos. 3,815,604, 3,884,238, 4,210,146 and 4,513,745.

SUMMARY OF THE INVENTION

An object of this invention is to provide a surgical suction cutting instrument which minimizes the possibility of vital structures such as nerves, vessels and dura or the specimen bag from entering the suction port.

A further object of this invention is to provide modifications which could be made to known surgical suction cutting instruments in a simple manner without requiring any significant redesign of the instrument.

In accordance with this invention the surgical suction cutting instrument includes a probe having a suction passage provided with a suction port so that the probe could be placed at the operative site to perform its cutting action. In accordance with the invention a guard is provided over the port to limit access through the port while still providing a sufficient open area to permit the desired cutting action to take place while preventing the vital structures from entering the port.

The guard may take various forms in accordance with this invention. Such forms could include, for example, a cage formed of spaced wires or metal ribbons which could be mounted in a bowed manner around the suction port or could lie flat against the instrument in a retracted state until their use is needed whereupon the guard could be activated so as to bow outwardly away from the port.

A BRIEF DESCRIPTION OF THE DRAWINGS

FIG. 1 is a side elevational view of a surgical suction instrument in accordance with one embodiment of this invention;

FIG. 2 is a side elevational view of the probe end of the instrument shown in FIG. 1;

FIG. 3 is a top plan view of the probe end of the instrument shown in FIG. 2;

FIG. 4 is a front elevational view of the probe end of the instrument shown in FIGS. 2–3;

FIG. 5 is a cross-sectional view taken through FIG. 3 along the line 5—5;

FIG. 6 is a cross-sectional view in elevation of the probe end of the instrument shown in FIGS. 3–5;

FIG. 7 is a side elevational view of a surgical suction cutting instrument in accordance with a further embodiment of this invention;

FIG. 8 is a top plan view of the instrument shown in FIG. 7;

FIG. 9 is a side elevational view of yet another embodiment of this invention with the guard in a retracted position;

FIG. 10 is a view similar to FIG. 9 showing the guard in its bowed condition;

FIG. 11 is a end elevational view of the instrument shown in FIG. 10;

FIG. 12 is a side elevational view partly in section of still yet another instrument in accordance with this invention;

FIG. 13 is an end elevational view of the instrument shown in FIG. 12; and

FIG. 14 is a cross sectional view in elevation of yet another embodiment of this invention.

DETAILED DESCRIPTION

The present invention generally involves the provision of a guard around the suction port at the probe end of a surgical suction cutting instrument to prevent vital structures such as nerves, vessels and dura or specimen bag from being drawn into the port and thereby damaged during the cutting operation. It is to be understood that the invention could be applied to various types of known surgical suction cutting instruments. Exemplary of these instruments are the types of devices described in U.S. Pat. Nos. 3,815,604, 3,884,238, 4,210,146 and 4,513,745 the details of which are incorporated herein by reference thereto. It is to be understood, however, that these patents simply represent exemplary type instruments which may be modified for incorporation of the invention. It is, however, not critical that the invention be used in any of these specific types of instruments.

FIGS. 1–6 illustrate a surgical suction cutting instrument 10 which could be used for disc aspiration. As shown therein instrument 10 includes a handle 12 and a probe 14 with a suction port 36 at the distal end of probe 14. A guard in a form of a cage 44 is located at port 36 and is bowed outwardly to permit access to port 36 at the operative area near dura 40. Suction applied by vacuum source 24 aspirates disc particles 40 back through passage 16 in probe 14 in a known manner. It is to be understood that instrument 10 is shown in very general form since different variations in details could be used to incorporate the invention herein.

In the illustrated embodiment the distal tip 48 of probe 14 is solid so that the port 36 is thus a side port.

As best shown in FIGS. 5–6 the particles 40 are aspirated through the open space provided by guard 44 into side suction port 36 and then into the hollow passageway 16 of probe 14. Suction applied from vacuum source 22 draws the material through passageway 16 and out of the instrument in a known manner. Any tissue in the area of the distal end of probe 14 is prevented from entering suction port 36 because of the location of guard 44 mounted outwardly of port 36. Thus, where used for disc aspiration, guard 44 would keep the dura from entering port 36 and thus being injured.

Guard 44 may take any suitable form and could be fixed and solid or could be formed by spaced wires or metal ribbons. In the illustrated embodiment guard 44 is formed as bowed portions or bars of a sleeve 45 mounted to the distal end of probe or needle 14.

Where in the illustrated embodiment the cage or guard 44 is comprised of two raised bars there is sufficient open area exposed from port 36 to permit tissue or the disc material 40 to be aspirated. The guard, effectively recesses the port when a structure tethered on both ends such as a vessel is sucked into the instrument. The guard effectively increases the distance to the cutting mechanism. If the height of the guard or the recess of the port is great enough the tethered ends of the material prevent the structure from reaching the cutting mechanism.

FIGS. 7-8 illustrate an alternative form of this invention wherein the surgical suction cutting instrument 10A may have generally the same structure as instrument 10. The difference, however, is in the form of guard. As shown therein the suction port 36 is provided with a guard 50 formed by a wire permanently mounted at each end 52 in any suitable manner on each port 36 so as to prevent complete direct access to port 36. The wire 50 could be a thin wire of circular cross-section or a flat strip of metal mounted over the center of port 36.

FIGS. 9-11 illustrate yet another surgical suction cutting instrument 10B in accordance with this invention. As shown therein the guard 54 is formed as a wire which is anchored at one end 56 to the distal end of probe 14B. The other end of the wire (not shown) is slidably mounted in a sleeve or guide 58 and may be manipulated at the proximal end of instrument 10B. The advantage of guard 54 is that it can be retracted as shown in FIG. 9 to be flat against the outer surface of probe 14B. Thus, the instrument 10B could be placed through a smaller cannula during the insertion process. Once instrument 10B is in place the proximal end of guard 54 would be activated to be moved in the direction of the arrow 58 so that the guard is bowed outwardly away from port 36 as shown in FIG. 10.

FIGS. 12-13 show yet another instrument 12C in accordance with this invention. As shown therein the probe 14 includes a blade 60 mounted at the end of drive shaft 62 in the manner of a known rotary cutter such as used as an arthroscopic shaver. The port 36C is located at the distal end of probe 14 by having the entire distal end open. Guard 64 is formed as a wire or band covering the distal end bowed outwardly from port 36.

FIG. 14 shows a variation of the invention wherein the probe 14 is provided with a cutting mechanism 66 wherein the port 36 is functionally recessed in relationship to the cutting mechanism 66.

It is to be understood that the invention may be practiced in its various embodiments such as embodiments of FIGS. 7-9, 10-11 and 12-13 where more than one wire or strip is used to form the guard. Similarly various embodiments showing side ports could use end ports and vice versa. It is also to be understood that features shown in any one embodiment could also be used in other embodiments within the concepts of this invention.

What is claimed is:

1. In a surgical suction cutting instrument including a hollow probe with a suction port at the distal end of said probe, a source of suction communicating with said probe and movable cutting structure disposed in said hollow probe and having a cutting edge adjacent said suction port for cutting tissue, the improvement being in that a guard is mounted over said suction port, said guard including an engaging portion dimensioned to limit access into said suction port and a passageway to provide a path for tissue into said suction port, the cutting structure defining a lumen in communication with said suction port and said source of suction to cut tissue portions.

2. The instrument of claim 1 wherein said guard is in the form of a cage having spaced ribs.

3. The instrument of claim 2 wherein said cage is part of a sleeve mounted to said probe.

4. The instrument of claim 1 wherein said suction port is a side port.

5. A surgical instrument which comprises:
   an elongated probe dimensioned for insertion within a small passageway in tissue, the probe defining a longitudinal axis and having proximal and distal end portions, and a lumen extending longitudinally therealong, an outer wall of the elongated probe having an opening defining a port for entry of tissue, the port in fluid communication with the lumen;
   a source of suction connected to the probe in fluid communication with the lumen; and
   a guard member mounted adjacent the distal end portion of the elongated probe, the guard member including at least one rib member extending at least over a portion of the opening in the outer wall, the one rib member defining a bowed portion extending at least radially outwardly from the opening to inhibit tissue from entering the opening while permitting limited access into the opening.

6. The surgical instrument according to claim 5 including a handle mounted to the elongated probe.

7. The surgical instrument according to claim 5 wherein the opening in the outer wall of the elongated probe is a radial opening.

8. The surgical instrument according to claim 7 wherein the guard member is a sleeve member, the sleeve member having the one rib member connected thereto, the sleeve member positioned about the elongated probe.

9. The surgical instrument according to claim 8 including a plurality of spaced rib members.

10. The surgical instrument according to claim 8 including cutting structure disposed in the elongated probe for cutting tissue entering the port.

11. The surgical instrument according to claim 10 wherein the cutting structure defines the lumen of the elongated probe.

12. The surgical instrument according to claim 5 including cutting structure disposed in the elongated probe for cutting tissue entering the port.

13. The surgical instrument according to claim 12 wherein the cutting structure is movable within the elongate probe and has a distal cutting surface.

14. A surgical instrument which comprises:
   an elongated probe dimensioned for insertion within a small passageway in tissue, the probe including an outer member defining a longitudinal axis and having proximal and distal end portions, an outer wall of the elongated probe having an opening defining a port for entry of tissue;
   a cutting member disposed in the elongated probe and movable therewithin, the cutting member defining a cutting edge for cutting tissue and having a lumen extending longitudinally therealong in communication with the port;
   a source of suction in fluid communication with the lumen; and
   a stationary guard member fixedly mounted to the distal end portion of the elongated probe, the guard member dimensioned to limit access into said suction port while still providing a path through said guard and into said suction port.

15. The surgical instrument according to claim 14 wherein the guard member includes an engaging portion dimensioned to limit access into said suction port and a passageway, the passageway defining the path through the guard for tissue to enter the port of the elongated probe.

16. The surgical cutting instrument according to claim 14 wherein the guard member includes at least one rib member extending at least over a portion of the opening in the outer wall, the one rib member defining a bowed portion extending at least radially outwardly from the opening to inhibit tissue from entering the opening while permitting limited access into the opening.

* * * * *